(12) United States Patent
Comstock et al.

(10) Patent No.: US 8,748,846 B2
(45) Date of Patent: Jun. 10, 2014

(54) PHOTOFRAGMENTATION-LASER-INDUCED FLUORESCENCE FOR DETECTION OF NITRIC OXIDE-BEARING EXPLOSIVES

(75) Inventors: Matthew Comstock, Orlando, FL (US); Matthew K. Fisher, Longwood, FL (US); Daniel E. Woody, Sumterville, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 127 days.

(21) Appl. No.: 13/313,378

(22) Filed: Dec. 7, 2011

(65) Prior Publication Data

US 2012/0145925 A1   Jun. 14, 2012

Related U.S. Application Data

(60) Provisional application No. 61/420,823, filed on Dec. 8, 2010.

(51) Int. Cl.
*G01J 1/58* (2006.01)
(52) U.S. Cl.
USPC .................. 250/458.1; 250/459.1; 250/461.1; 250/372
(58) Field of Classification Search
USPC .......................... 250/458.1, 459.1, 461.1, 372
See application file for complete search history.

(56) References Cited

U.S. PATENT DOCUMENTS 5,728,584 A * 3/1998 Sausa et al. .................... 436/106
7,933,013 B2   4/2011 Li 2003/0133096 A1 * 7/2003 Aroussi et al. ................... 356/28
2008/0266659 A1 * 10/2008 Ulrich et al. .................... 359/387
2009/0290142 A1 * 11/2009 Li ................................... 356/51
2010/0047916 A1   2/2010 Rothschild et al.

OTHER PUBLICATIONS

Boudreaux et al., Development of a photofragmentation laser-induced-fluorescence laser sensor for detection of 2,4,6-trinitrotoluene in soil and groundwater, Mar. 20, 1999, Applied Optics, vol. 38, pp. 1411-1417.*
Heflinger et al., Application of a unique scheme for remote detection of explosives, Apr. 1, 2002, Optics Communications, vol. 204, pp. 327-331.*
Wynn et al., A Novel Method for Remotely Detecting Trace Explosives, 2008, Lincoln Laboratory Journal, vol. 17, pp. 1-13.*
Settersten et al., "Radiative lifetimes of NO $A^2\_+, v\_=0,1,2...$ and the electronic transition moment of the $A^2\_+ X^2\_$ system," Sep. 1, 2009, The Journal Of Chemical Physics, pp. 1-3.*

(Continued)

*Primary Examiner* — Christine Sung
(74) *Attorney, Agent, or Firm* — Terry M. Sanks, Esq.; Beusse Wolter Sanks Mora & Maire, P.A.

(57) ABSTRACT

A method for identifying a presence of a nitro (NO)-bearing compound suspected of being included in a sample includes photodissociating a sample into one or more fragments that include a NO molecule, where the NO molecule has an electron in a first-vibrational excited state of an electronic ground state. Laser-induced fluorescence (LIF) is applied including directing UV light from a UV laser source at the sample to induce fluorescent light. An emission wavelength of 270 nm to 274 nm from fluorescent light received is used to identify a presence of the NO-bearing compound in the sample.

11 Claims, 3 Drawing Sheets

(56) References Cited

OTHER PUBLICATIONS

Thomas A. Reichardt, et al., "Photofragmentation Approaches for the Detection of Polyatomic Molecules", CLEO Conference Paper, Conference on Lasers and Electro-Optics OSA Technical Digest, San Jose, CA, May 16, 2010, Chemical/Biological/Medical Sensing (CTuB), Optical Society of America.

Stephen D. Roberson, et al., Laser-Based Detection of TNT and RDX Residues in Real Time Under Ambient Conditions, Applied Spectroscopy, vol. 64, No. 7, pp. 760-766, 2010.

* cited by examiner

PHOTOFRAGMENTATION-LASER-INDUCED FLUORESCENCE FOR DETECTION OF NITRIC OXIDE-BEARING EXPLOSIVES

CROSS REFERENCE TO RELATED APPLICATIONS

This application claims the benefit of Provisional Application Ser. No. 61/420,823 entitled "PHOTOFRAGMENTATION-LASER-INDUCED FLUORESCENCE FOR DETECTION OF NITRIC OXIDE-BEARING EXPLOSIVES" filed Dec. 8, 2010, which is herein incorporated by reference in its entirety.

FIELD

Disclosed embodiments relate to photofragmentation laser-induced fluorescence (PF-LIF) detection of materials, particularly nitric oxide-bearing compounds, that may be present in materials such as explosives.

BACKGROUND

There is a strong demand for systems or sensors that can detect the presence of hazardous materials, such as explosive materials, particularly those with high sensitivity and specificity, as well as the capability for standoff detection. Primary, secondary and tertiary explosives make up the three classes of high explosive materials, each having decreasing sensitivity to shock, friction, and heat. Peroxide-based explosives (e.g., acetone peroxides) are one of the main constituents of primary explosives, while nitro-based explosives make up the majority of secondary explosives (e.g., trinitrotoluene (TNT), cyclotrimethylenetrinitramine (RDX), pentrite (PETN), while tertiary explosives include ammonium nitrate/fuel oil (e.g., ANFO).

Direct detection of explosives using native fluorescence of the target substance is difficult because the fluorescence spectra are typically broad and structureless/featureless. Selective photofragments from photodissociation of explosive materials have strong fluorescence that produces structured or feature-evident spectra. Nitric oxide (NO) is a characteristic photofragment of nitro-based explosive materials when the explosive material is irradiated with ultraviolet (UV) light. Specifically, absorption by NO via its various A-X (v',v") bands, e.g. (0,0), (1,1), (2,2), and (0,2) is known to have transitions near 226, 224, 222, and 248 nm, resulting in discrete characteristic laser-induced fluorescence (LIF) emissions.

Typically LIF measurements are performed using 226 nm laser excitation. However, 226 nm excitation is plagued by a background of natural NO in the air, making it difficult to detect low vapor pressure compounds such as certain explosives (e.g., 2,4,6 trinitrotoluene (TNT)), which may have a concentration from around 1 to 10 parts per billion (PPB) in typical samples. Most nitro-based explosives have a low NO vapor pressure that combined with the low concentration in the sample generally results in a low signal level for the LIF signal emanating from the sample. Another known option is to use 236 nm laser excitation, and to detect fluorescent emission peaks at 226 nm or 247 nm, which represent the NO peaks having the highest and second highest relative signal strengths in the conventional spectral range of interest for PF-LIF for nitro-based explosives, being from 200 to about 250 nm.

Problems with known PF-LIF systems for NO-based explosives include detectability problems and low throughput due to low emission signal levels at the photodetector due to the low signal level of interest emanating from the sample combined with the signal loss through the spectral filter (low % transmission of the emission signal transmitted) before detection at the photodetector. A highly attenuating spectral filter is required in conventional PF-LIF systems due to the need to selectively detect the emission peak of interest at 226 nm or 247 nm while rejecting the closely spaced laser peak in the wavelength range about 225 nm to 250 nm. Moreover, interference from atmospheric $O_2$ fluorescence can confuse signal analysis both within the wavelength range from about 225 nm to 250 nm, and outside this wavelength range.

SUMMARY

Disclosed embodiments recognize conventional photofragmentation laser-induced fluorescence (PF-LIF) detection of NO-based explosive materials using 226 nm or 236 nm laser excitation and 247 nm or 226 nm emission wavelengths being close in the spectrum results in detectability problems and/or low throughput due to low emission signal levels detected by the photodetector. As noted above, available filter technology is highly attenuating to provide the required spectral selectivity between close peaks (e.g. within about 10 nm) which results in low throughput, such as $\leq 1\%$ emission signal transmission through available spectral filters, and need for short standoff distances.

Disclosed embodiments instead are based on identifying the presence of NO-based explosive materials using the NO emission line between 270 nm and 274 nm, centered at about 271.5 nm, which is spectrally further from the NO and $O_2$ emission peaks that allows use of substantially more transmissive filters (e.g., $\geq 10\%$ transmission) which raises the emission signal levels detected at the photodetector compared to conventional PF-LIF NO-based explosive detection systems despite its low relative emitted signal strength as compared to 247 nm or 226 nm emission peaks (see FIG. 1 described below). Moreover, the 270 nm to 274 nm peak is also well within the solar blind UV region of the electromagnetic spectrum, so that the background signal is very low.

DETAILED DESCRIPTION

Figure 1:
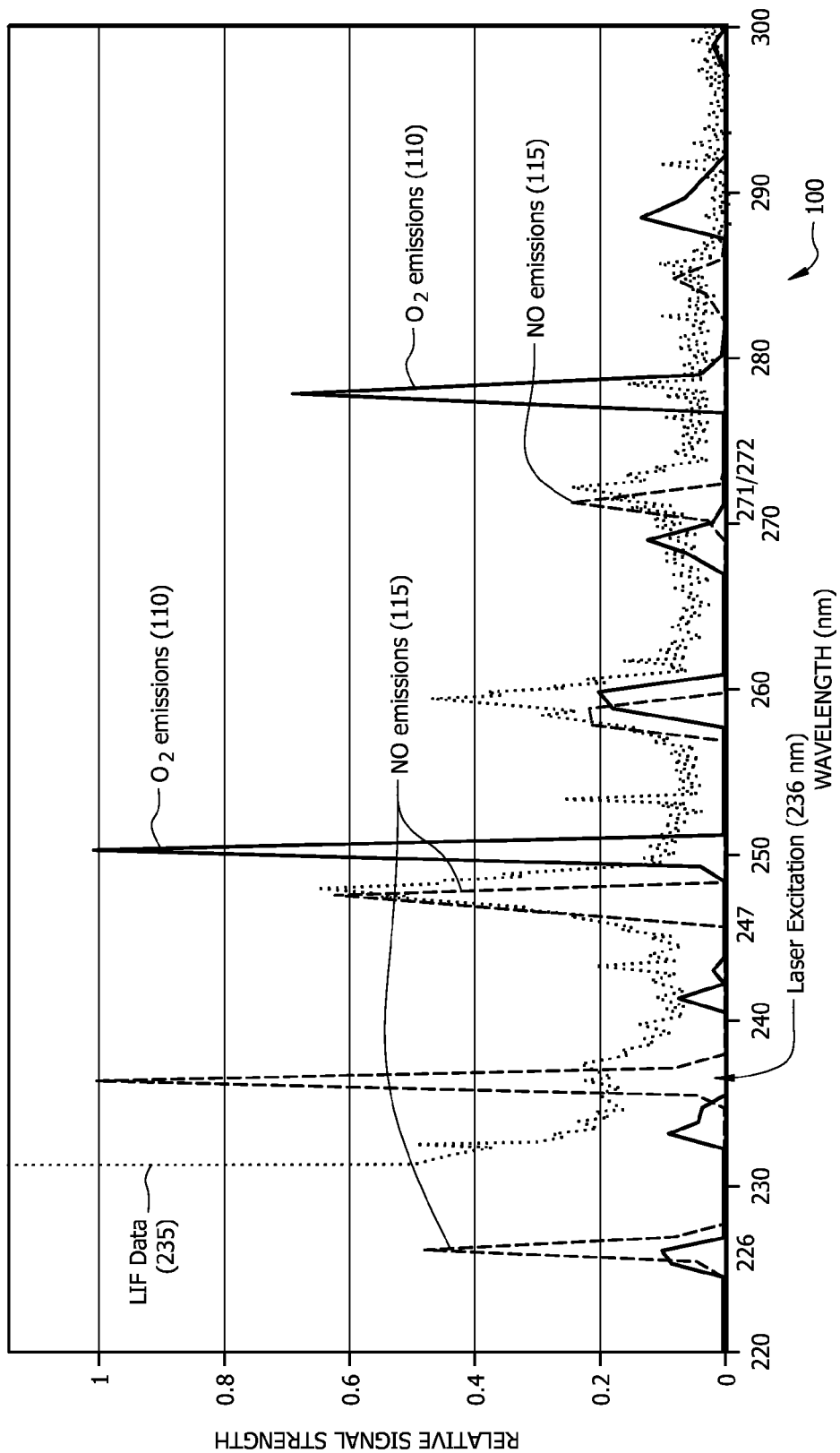
FIG. 1 is a depiction of an example actual LIF spectrum from 230 nm to 300 nm for trinitrotoluene (TNT) in air showing superimposed $O_2$ emission peaks, NO emission peaks from 220 to 300 nm, with the NO peak shown at 271-272 nm used for disclosed embodiments highlighted, according to an example embodiment.

Disclosed embodiments are described with reference to the attached figures, wherein like reference numerals, are used throughout the figures to designate similar or equivalent elements. The figures are not drawn to scale and they are provided merely to illustrate aspects disclosed herein. Several disclosed aspects are described below with reference to example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. Disclosed embodiments are not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

PF-LIF, upon which disclosed embodiments are based, is first reviewed herein. In a first step, a first photon from an electromagnetic wave source, typically a laser source, is absorbed by a sample suspected of including a solid (e.g. powder) NO-based target molecule of interest, such as TNT. If the target molecule is present, some of the target molecule vaporize, and dissociate into a plurality of fragments, including fragments having vibrationally excited NO. In a second step, a second photon from a laser source, pumps the vibrationally excited NO into an electronically excited state. As known in the art, the first and second step may be combined. In a third step, the NO molecule in the electronically excited state fluoresces as it returns to its ground state, resulting in the emission of signals at a plurality of different wavelengths. The identification can include distinguishing the substance (e.g., parent molecule) from one or more other types of materials having a NO portion (e.g., an atmospheric NO-containing compound, an inorganic NO-containing compound, and fertilizer).

One disclosed embodiment comprises a PF-LIF-based method for identifying the presence of a NO-bearing compound suspected of being in a sample. The method includes photodissociating a sample into one or more fragments that include a NO molecule, wherein the NO molecule has an electron in a first-vibrational excited state of an electronic ground state. LIF is employed to induce fluorescent light from the NO molecule. The fluorescent light is detected at the emission line at 270 nm to 274 nm to identify a presence of the NO-bearing compound in the sample.

As noted above, one advantage of disclosed embodiments is that the 270 nm to 274 nm emission line is well within the "solar blind UV region". When solar radiation transmits in the atmosphere, the radiation wave band from about 240 nm to 280 nm is strongly absorbed by the ozone layer, which makes the atmospheric ultraviolet radiation in this wave band very low level since it is difficult for 240 nm to 280 nm radiation to reach the near earth's surface, thus lowering background noise.

The excitation wavelength for LIF for disclosed embodiments can be at 236 nm. 247 nm excitation can also be used, although the signal is emission signal levels are generally significantly lower as compared to than that produced by 236 nm excitation due to a lower thermal population.

FIG. 1 is a depiction 100 of an actual LIF spectrum using the PF-LIF detection system 200 shown in FIG. 2 described below from 230 nm to 300 nm including LIF data 235 for trinitrotoluene (2,6-dinitrotoluene; TNT) in air. Also superimposed is $O_2$ emission data 110 and NO emission data 115 from 220 to 300 nm including conventional peaks at 226 nm and 247 nm, with the NO peak at 270 nm to 274 nm shown at 271 nm/272 nm used for disclosed embodiments highlighted. The laser excitation line is shown at 236 nm. The LIF data 235 cuts off below 230 nm because of the strength of the 226 nm emission from natural NO in the air (the detector saturates).

The spectral distance between the 236 nm laser excitation line and the 270 nm to 274 nm LIF line used for disclosed detection is about 35 nm. In contrast, the spectral distance between the 236 nm laser excitation line and the 226 nm and 247 nm NO lines are both about 10 nm. Moreover, as noted above, the 270 nm to 274 nm LIF line is well within the solar blind UV region, which lowers background noise. In addition, the 270 nm to 274 nm LIF line can be seen to be a few nm (about 3 nm) away from the closest $O_2$ line.

The NO-bearing target can comprise, for example, TNT, cyclotrimethylenetrinitramine (RDX), pentrite (PETN), and tertiary explosives (such as ammonium nitrate/fuel oil (ANFO)). Another substance that can be identified using disclosed embodiments is urea nitrate, which can be found in fertilizer-based high explosives. The NO-based target molecule can be present in an unknown sample (e.g., material disposed on a substrate surface in a solid form), which is to be identified.

Figure 2:
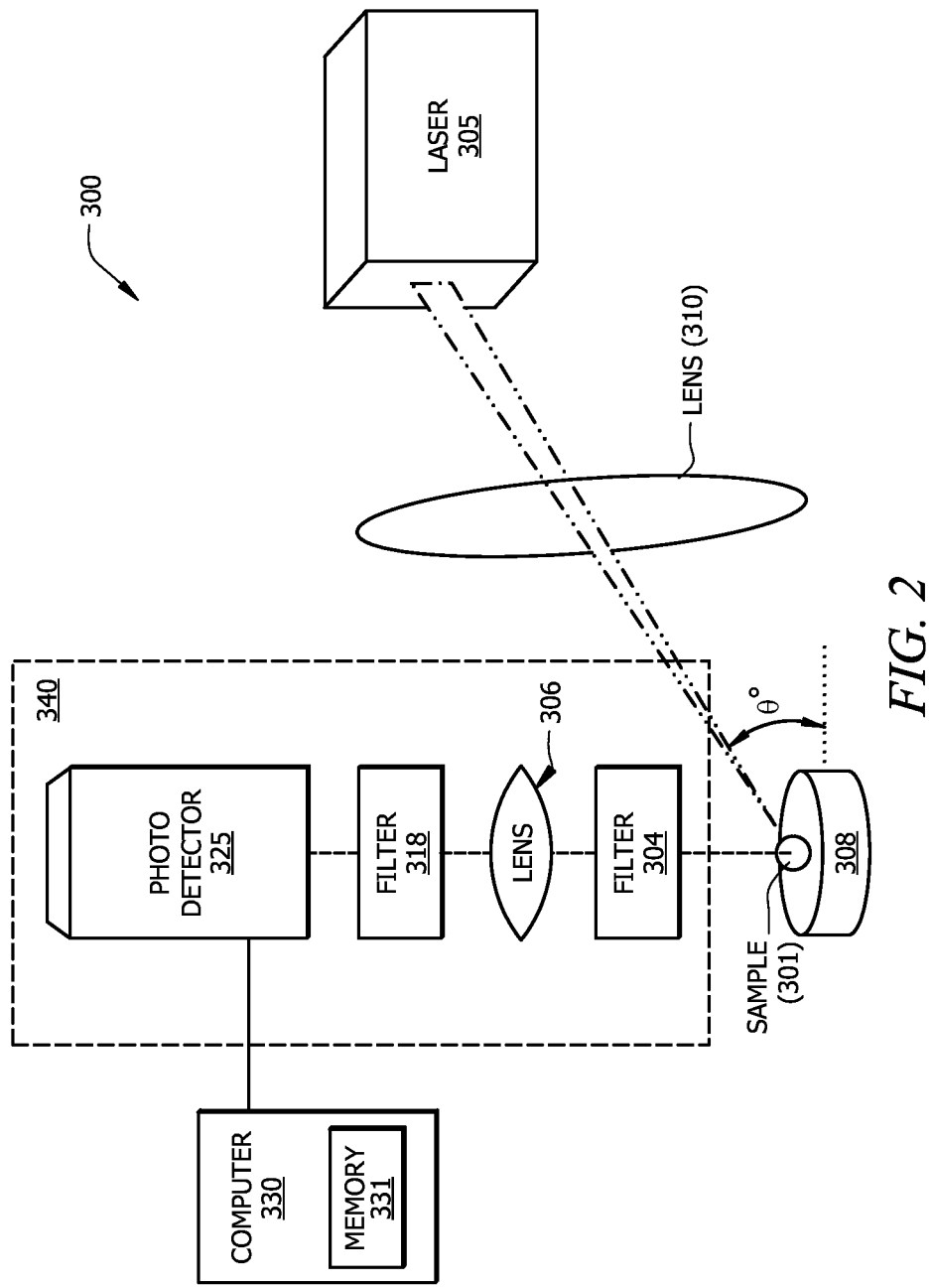
FIG. 2 is a schematic diagram of an example system for PF-LIF for detection of NO bearing explosives, according to an example embodiment.

FIG. 2 is a schematic diagram of an example PF-LIF detection system 200 for detecting NO bearing explosive materials, according to an example embodiment. System 300 includes a laser source 305 and an optional lens 310 shown for irradiating a sample 301 suspected of having a target NO-bearing compound, and a collection optics subsystem 340.

The laser source 305 is operable to produce a beam of UV light at a wavelength that will induce photofragmentation of target molecules. For example, the laser source 305 may be a type that produces a laser beam of UV light at 236 nm to target NO-based explosive materials.

The laser 305 can be a pulsed laser providing a pulsed output, such as having a repetition rate of 20 to 50 Hz, and a pulse length less than about 10 nsec. The pulsed laser can comprise a Q-switched laser, a cavity-dumped laser, a gain-switched laser, an amplified time-gated continuous wave laser, and a gated long-pulse laser. In one embodiment, the pulsed laser comprises a passively Q-switched Nd:YAG laser. Additionally, the laser 305 can be part of a laser system that can comprise one or more nonlinear elements to convert the laser emission at one wavelength to another wavelength, such as to output 236 nm UV light.

The collection optics subsystem 340 captures the fluorescence emissions from target in the sample 301 which is on the surface 308 shown, or the sample can be in some other space. Although not shown, the collection optics subsystem 340 can couple the captured LIF emissions from the sample 301 via an optical fiber to the spectral filter for selectively detecting the 270 nm to 274 nm line shown as light dispersive element 318.

Collection optics subsystem 340 is shown including a bandpass filter 304 that eliminates detection of Raman scattering associated with the beam from the laser source 305. The laser source 305 can be positioned offset from the collection optics subsystem 340, or positioned directly in front of the collection optics subsystem 340. Collection optics subsystem 340 is also shown including a lens 306 to collimate light emitted by the sample 301, and a filter 318 for transmitting the 270 to 274 nm line to the photodetector 325.

The filter 318 can comprise a dispersive or non-dispersive filter. In one embodiment filter 318 comprises a dispersive filter (e.g., grating or prism) that disperses the collimated light into its constituent wavelengths according to the refractive properties of the dispersive element. Dispersive filter generally includes a slit and a secondary lens that processes the light before the light reaches the grating or prism. For example, the dispersive filter may comprise a diffraction grating that spans a spectral range of approximately 40 nm.

In another embodiment filter 318 comprises a non-dispersive filter, such as a custom bandpass filter. An example custom bandpass filter comprises a custom designed dielectric stack on silica or some other transparent substrate. Such a bandpass filter can make the overall system both simpler and smaller, and increase the overall system efficiency as compared to when the filter 318 comprises a dispersive filter.

The photodetector 325 generates fluorescence spectra from the dispersed fluorescence. Photodetector 325 can comprise an intensified CCD (ICCD) detector which has a built-in image intensifier in front of the CCD sensor to multiply the light signal into the detector.

The computer 330 shown can include signal processing electronics having associated memory 331, which is coupled to the photodetector 325. The computer 330 analyzes the fluorescent light spectra obtained by executing one or more software programs stored in the memory, such as memory 331, to compare the fluorescence spectra against the library of spectra data stored in the data storage unit. More generally, the functions of the computer 330 to analyze the fluorescence spectra may be implemented by logic encoded in one or more tangible media (e.g., embedded logic such as an application specific integrated circuit, digital signal processor (DSP) firmware instructions, software that is executed by a processor, etc.).

The computer 330 may include the memory 331 as shown or access separately memory and a data storage unit containing a library of spectra data. As one example, the system 200 may be configured to detect explosive materials. However, the system 200 may also be configured to detect other types of substances that are not explosive materials.

Disclosed PF-LIF detection systems can be used in a variety of applications. For example, expected applications include airport screening, mass transit screening, courthouse screening and stadium screening.

EXAMPLES

Disclosed embodiments are further illustrated by the following specific Example, which should not be construed as limiting the scope or content of this Disclosure in any way.

Figure 3:
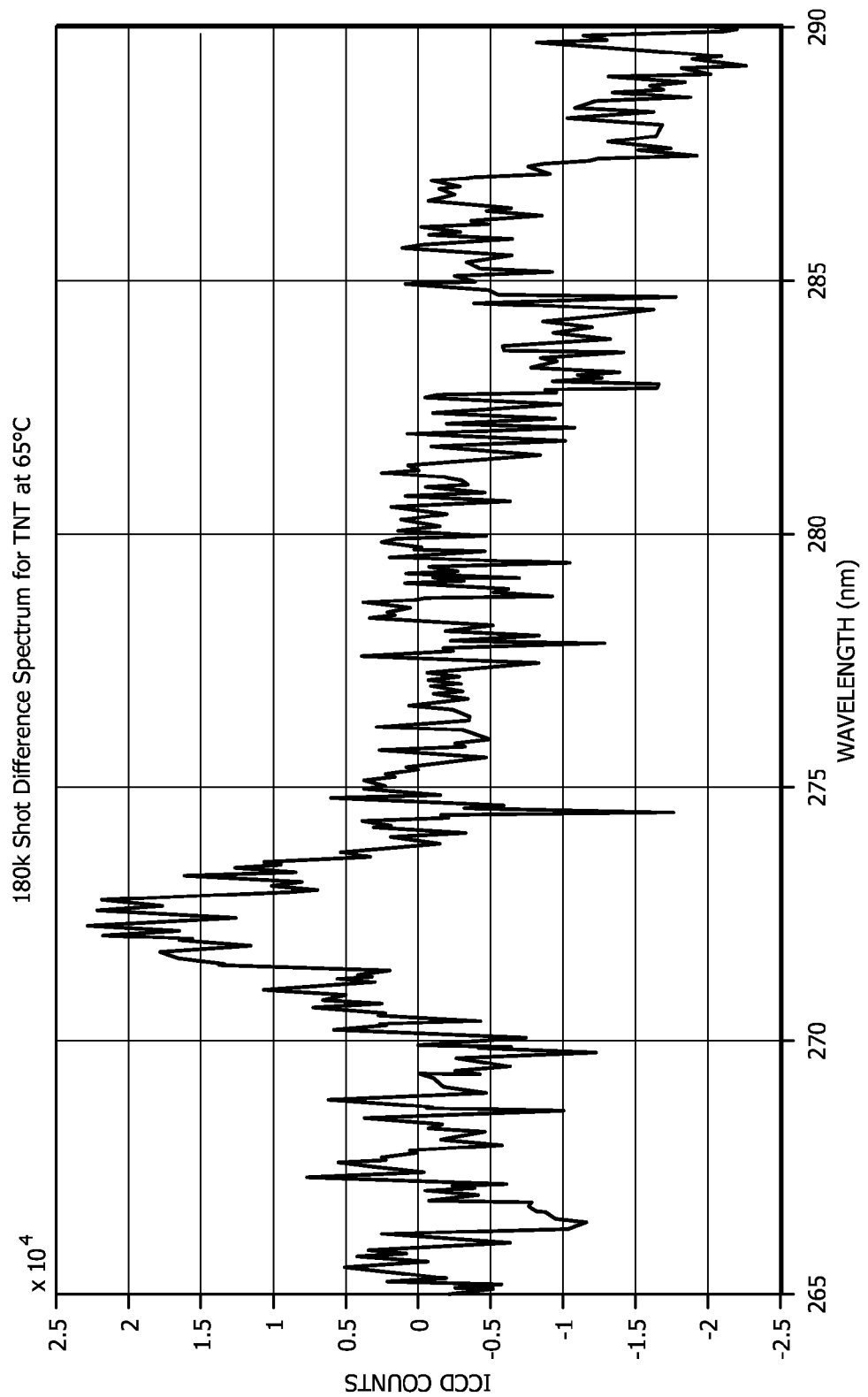
FIG. 3 shows a 180k shot difference LIF spectrum for TNT at 65° C., according to an example embodiment.

FIG. 3 shows a 180k shot difference PF-LIF spectrum obtained using an example system for PF-LIF detection of NO bearing explosive materials analogous to system 200 shown in FIG. 2 including an ICCD detector for detection of TNT at 65° C., according to an example embodiment. A "180k shot difference" stands for data obtained from 180,000 accumulated laser pulses with the sample present minus (subtracted from) 180,000 accumulated laser pulses with the TNT sample absent.

The PF-LIF spectrum was collected at a 36 m standoff distance. In contrast, known PF-LIF systems due to their low signal levels are generally limited to standoff distances of 2 m or less. ICCD detector counts are shown from 265 nm to 290 nm, with a large relative peak at around 271/272 nm. The spectrometer used to provide the data shown comprised a dispersive spectrometer. However, as noted above, a non-dispersive filter such as a custom bandpass filter can replace the dispersive spectrometer which can make the overall system both simpler and smaller, and increase the overall system efficiency.

While various disclosed embodiments have been described above, it should be understood that they have been presented by way of example only, and not as a limitation. Numerous changes to the disclosed embodiments can be made in accordance with the Disclosure herein without departing from the spirit or scope of this Disclosure. Thus, the breadth and scope of this Disclosure should not be limited by any of the above-described embodiments. Rather, the scope of this Disclosure should be defined in accordance with the following claims and their equivalents.

Although disclosed embodiments have been illustrated and described with respect to one or more implementations, equivalent alterations and modifications will occur to others skilled in the art upon the reading and understanding of this specification and the annexed drawings. While a particular feature may have been disclosed with respect to only one of several implementations, such a feature may be combined with one or more other features of the other implementations as may be desired and advantageous for any given or particular application.

The terminology used herein is for the purpose of describing particular embodiments only and is not intended to be limiting to this Disclosure. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this Disclosure belongs. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

We claim:

1. A method for identifying a presence of a nitro (NO)-bearing compound suspected of being included in a sample, comprising:
   photodissociating a sample into one or more fragments that include a NO molecule, said NO molecule having an electron in a first-vibrational excited state of an electronic ground state;
   employing laser-induced fluorescence (LIF) comprising directing UV light from a UV laser source at said sample to induce emission of fluorescent light; and
   detecting said fluorescent light at an emission wavelength of 270 to 274 nm to identify a presence of said NO-bearing compound in said sample, wherein said detecting comprises shot differencing including: generating a first plurality of shots having said sample present, generating a second plurality of shots not having said sample present, and obtaining difference signals by subtracting counts from said second plurality of shots from counts obtained from said first plurality of shots.

2. The method of claim 1, wherein said UV laser source comprises a pulsed laser.

3. The method of claim 1, wherein said NO-bearing compound comprises at least one of 2,6-dinitrotoluene, 2,4,6 trinitrotoluene, pentaerythritol tetranitrate, hexahydro-1,3,5-trinitro-1,3,5-triazine, and cyclotrimethylenetrinitramine, and urea nitrate.

4. The method of claim 1, wherein said detecting comprises filtering using a non-dispersive filter.

5. The method of claim 1, wherein said detecting comprises filtering using a dispersive filter.

6. The method of claim 1, wherein an intensified CCD (ICCD) detector is used for said detecting.

7. A system for detection of nitric oxide-bearing explosives, comprising:
- a source of electromagnetic radiation for photodissociating a sample suspected of including a nitro (NO)-bearing compound into one or more fragments that include a NO molecule, said NO molecule having an electron in a first-vibrational excited state of an electronic ground state;
- a UV laser source providing an excitation wavelength for employing laser-induced fluorescence (LIF) to induce emission of fluorescent light;
- a filter positioned to receive said fluorescent light for selectively transmitting a band including a wavelength at 270 nm to 274 nm or dispersing at least a portion of said fluorescent light including said wavelength at 270 nm to 274 nm;
- a photodetector coupled to an output of said filter for detecting said wavelength at around 270 to 274 nm; and
- a computer coupled to an output of said photodetector for identifying a presence of said NO-bearing compound in said sample, wherein said computer is configured to perform a shot differencing comprising:
- acquiring data under a first plurality of shots with said sample present,
- acquiring data under a second plurality of shots without said sample present, and
- calculating a difference between the data acquired under the first plurality of shots and the data acquired under the second plurality of shots, said difference indicative of the presence of said NO-bearing compound.

8. The system of claim 7, wherein said UV laser source comprises a pulsed laser.

9. The system of claim 7, wherein said filter comprises a non-dispersive filter.

10. The system of claim 7, wherein said filter comprises a dispersive filter.

11. The system of claim 7, wherein said photodetector comprises an intensified CCD (ICCD) detector.

* * * * *